United States Patent [19]

Fukao et al.

[11] Patent Number: 5,097,088
[45] Date of Patent: Mar. 17, 1992

[54] PROCESS FOR PREPARING ALKYL-SUBSTITUTED AROMATIC HYDROCARBON

[75] Inventors: Masami Fukao, Shiga; Takuo Hibi, Osaka; Kiyoshi Ikimi, Oita; Gohfu Suzukamo, Osaka, all of Japan

[73] Assignee: Sumitomo Chemical Company, Limited, Osaka, Japan

[21] Appl. No.: 586,074

[22] Filed: Sep. 21, 1990

[30] Foreign Application Priority Data

Jan. 30, 1990 [JP] Japan .................................. 2-020989

[51] Int. Cl.$^5$ ................................................ C07C 2/72
[52] U.S. Cl. ...................................... 585/453; 585/452
[58] Field of Search ............................... 585/542, 543

[56] References Cited

U.S. PATENT DOCUMENTS

| 2,769,850 | 11/1956 | Clossen et al. ............... 585/452 |
| 2,771,495 | 11/1956 | Pines et al. ............... 585/453 X |
| 2,780,660 | 2/1957 | Field et al. ............... 585/452 X |
| 3,251,895 | 5/1966 | Wilkes ............... 585/453 X |
| 3,691,241 | 9/1972 | Kamienski et al. ............... 585/452 X |
| 4,511,748 | 4/1985 | Kudoh et al. ............... 585/452 X |
| 4,720,601 | 1/1988 | Suzukamo et al. ............... 585/377 |
| 4,929,783 | 5/1990 | Smith ............... 585/452 |
| 4,977,124 | 12/1990 | Smith ............... 585/452 X |

FOREIGN PATENT DOCUMENTS

| 522628 | 3/1956 | Canada ............... 585/452 |
| 0328940 | 8/1989 | European Pat. Off. . |
| 0354584 | 2/1990 | European Pat. Off. . |
| 53229 | 3/1986 | Japan . |
| 902043 | 6/1962 | United Kingdom ............... 585/452 |
| 1259535 | 1/1972 | United Kingdom . |
| 1269280 | 4/1972 | United Kingdom . |

OTHER PUBLICATIONS

Pines et al., J. Am. Chem. Soc., 78:4316–4322 (1956).

*Primary Examiner*—W. J. Shine
*Assistant Examiner*—Douglas J. McGinty
*Attorney, Agent, or Firm*—Birch, Stewart, Kolasch & Birch

[57] ABSTRACT

An alkyl-substituted hydrocarbon is prepared by alkylating an alkylaromatic hydrocarbon having at least one hydrogen atom on an alpha-carbon in a side chain with an olefin in the presence of a solid base which is obtainable by treating an alumina with at least one compound of an alkaline earth metal at a temperature of from 200° to 800° C. and then with at least one compound selected from the group consisting of an alkali metal and an alkali metal hydride in an inert gas at a temperature of from 200° to 800° C.

19 Claims, No Drawings

PROCESS FOR PREPARING ALKYL-SUBSTITUTED AROMATIC HYDROCARBON

BACKGROUND OF THE INVENTION

1. Field of the Invention

The present invention relates to a process for preparing an alkyl-substituted aromatic hydrocarbon. More particularly, the present invention relates to a process for preparing an alkyl-substituted aromatic hydrocarbon by reacting an alkylaromatic hydrocarbon having at least one hydrogen atom on an alpha-carbon in said alkyl side chain with an olefin in the presence of a solid base which is obtainable by treating an alumina with at least one compound of an alkaline earth metal in a specific temperature range and successively with at least one compound selected from the group consisting of alkali metals and alkali metal hydride in an inert gas at a specific temperature range, whereby the alpha-position of the alkyl group is alkylated.

2. Description of the Related Art

The alkyl-substituted aromatic hydrocarbons are useful as intermediates in the production of fine chemicals such as agricultural chemicals, medicines and other chemicals and prepared by reacting the alkylaromatic hydrocarbon having the hydrogen atom on the alpha-carbon in the side chain with an olefin in the presence of a base catalyst.

As the preparation process of the alkyl-substituted aromatic hydrocarbon, there are known a process which utilizes a catalyst comprising metal sodium and chlorotoluene and a process which utilizes a catalyst comprising metal sodium supported on potassium carbonate (cf. J. Am. Chem. Soc., 78, 4316 (1956), GB Patent No. 1269280 and Japanese Patent Kokai Publication No. 53229/1986).

However, the conventionally used catalysts have various drawbacks such as insufficient catalytic activities, a low yield of the alkyl-substituted hydrocarbon per unit amount of the catalyst and troublesome separation of the catalysts from the product. Further, the conventional catalysts suffer from such problems in that when they are in contact with the oxygen and/or moisture in the air, they tend to lose their activities or they are ignited.

SUMMARY OF THE INVENTION

One object of the present invention is to provide a base catalyst which effectively catalyzes the reaction of the alkylaromatic hydrocarbon having the hydrocarbon atom on the alpha-carbon in the side chain with the olefin and can be easily separated from the product after the reaction.

Another object of the present invention is to provide a process for producing an alkyl-substituted hydrocarbon by reacting the alkylaromatic hydrocarbon having the hydrogen atom on the alpha-carbon in the side chain with the olefin.

Accordingly, the present invention provides a process for preparing an alkyl-substituted hydrocarbon comprising alkylating an alkylaromatic hydrocarbon having at least one hydrogen atom on an alpha-carbon in a side chain with an olefin in the presence of a solid base which is obtainable by treating an alumina with at least one compound of an alkaline earth metal at a temperature of from 200° to 800° C. and then with at least one compound selected from the group consisting of an alkali metal and an alkali metal hydride in an inert gas at a temperature of from 200° to 800° C.

DETAILED DESCRIPTION OF THE INVENTION

The process of the present invention is characterized in the use of the specific solid base as a catalyst, which solid base is prepared by treating the alumina with at least one compound of an alkaline earth metal at a temperature of from 200° to 800° C. and then with at least one compound selected from the group consisting of an alkali metal and an alkali metal hydride in an inert gas at a temperature of from 200° to 800° C.

As the alumina, various types of aluminas are used, except $\alpha$-alumina. Preferred examples of the alumina are $\gamma$-alumina, $\chi$-alumina and $\rho$-alumina. Among the alumina, those having a relatively large surface area are preferred.

In the preparation of the solid base, preferably the alumina is treated with the compound of alkaline earth metal and then the resulting product is further treated with the alkali metal and/or the alkali metal hydride in the inert gas atmosphere.

As the compound of alkaline earth metal, an oxide, a hydroxide, an alkoxide and an acetate of alkaline earth metal such as magnesium oxide, calcium oxide, barium oxide, magnesium hydroxide, calcium hydroxide, barium hydroxide, magnesium alkoxide, calcium alkoxide, barium alkoxide, magnesium acetate, calcium acetate and barium acetate are used. Mixtures of two or more compounds of the alkaline earth metal(s) may also be used. Among these compounds, the oxide and the hydroxide of alkaline earth metals are preferred. More preferably, magnesium oxide, magnesium hydroxide, calcium hydroxide, barium hydroxide and magnesium acetate are used.

The amount of the compound of the alkaline earth metal used is generally from 5 to 40% by weight based on the weight of the alumina.

For the purpose of treating the alumina with the alkaline metal earth compound, a solution or dispersion of said compound is poured on the alumina at the above specific temperature while stirring, or the alumina is immersed in the solution or dispersion to obtain the alumina carrying the compound thereon. Then, the alumina carrying the compound is treated by heating the alumina with said compound. Alternatively, when the alkaline earth metal compound is molten at the specific temperature at which the alumina is treated with the compound, a mixture of the compound and the alumina is treated by heating the alumina with the compound.

As the alkali metal or its hydride, an alkali metal of Group I of the Periodic Table such as lithium, sodium, potassium and rubidium or its hydride is used. They may be used as a mixture. Among these, sodium, potassium, sodium hydride, potassium hydride, or a mixture thereof, particularly, potassium and its hydride are preferred. The amount of the alkali metal or its hydride is generally from 2 to 15% by weight based on the weight of the alumina.

As the inert gas, nitrogen, helium, argon and the like are used.

In the preparation of the solid base to be used in the process of the present invention, the treatment temperature is important. Usually, the treatment temperature is from 200° to 800° C. Preferably, the alumina is treated with the compound of alkaline earth metal at a temperature range of 250° to 600° C., and the resulting product is treated with the alkali metal and/or its hydride at a temperature range of 200° to 450° C.

The treatment time varies with other treatment conditions, such as the treatment temperature. The treatment of the alumina with the compound of alkaline earth metal may be completed within 0.5 to 10 hours, and the treatment with the alkali metal and/or its hydride may be completed within 10 to 300 minutes.

By the use of the above treatments, the solid base which has high catalytic activity, good flowability and handleability can be obtained.

In the process of the present invention, the alkylaromatic hydrocarbon having the hydrogen atom on the alpha-carbon in the side chain is reacted with the olefin in the presence of the above described solid base as the catalyst.

As such alkylaromatic hydrocarbon, not only monocyclic aromatic hydrocarbons, but also condensed polycyclic aromatic hydrocarbons may be used. In the aromatic hydrocarbons, the side chains may be closed to form a ring. Specific examples of the alkylaromatic hydrocarbon are toluene, ethylbenzene, isopropylbenzene (cumene), n-propylbenzene, n-butylbenzene, sec.-butylbenzene, isobutylbenzene, xylene, cymene, diisopropylbenzene, methylnaphthalene, tetrahydronaphthalene, indan and the like. Among these, toluene, ethylbenzene and isopropylbenzene are preferred.

As the olefin, those having 2 to 20 carbon atoms are usually used. The olefin may by straight or branched. The carbon-corbon double bond may be a terminal or internal double bond. Preferably, the olefin having the terminal double bond is used. Specific examples of the olefin are ethylene, propylene, 1-butene, 2-butene, isobutylene, 1-pentene, 2-pentene, 1-hexene, 2-hexene, 3-hexene, 1heptene, 2-heptene, 3-heptene, octene, nonene, 3-methyl-1-butene, 2-methyl-2-butene, 3-methyl-1-pentene, 3-methyl-2-pentene and the like. Among these, ethylene, propylene, 1-butene and 2-butene are preferred.

The alkylation reaction according to the present invention may be carried out batchwise or continuously with the use of a fluidized bed or a fixed bed.

The reaction temperature for the alkylation is usually from 0° to 300° C., preferably from 20° to 200° C.

The reaction pressure is from atmospheric pressure to 200 kg/cm$^2$, preferably from 2 to 100 kg/cm$^2$.

The molar ratio of the olefin to the alkylaromatic hydrocarbon is usually from 0.1 to 10, preferably from 0.2 to 5.

In the batchwise reaction, the amount of solid base catalyst to be used is from 0.01 to 20% by weight based on the weight of the alkylaromatic hydrocarbon. The reaction time is generally from 0.5 to 50 hours, preferably from 1 to 25 hours.

In the continuous reaction, the mixture of the alkylaromatic hydrocarbon and the olefin in the above molar ratio is supplied at LHSV of 0.1 to 100 hr$^{-1}$, preferably 0.5 to 50 hr$^{-1}$.

According to the present invention, the alkyl-substituted hydrocarbon is effectively prepared in the presence of the solid base catalyst in a small amount under mild conditions. Further, the catalyst to be used according to the present invention is easily handled and is post-treated after the reaction.

PREFERRED EMBODIMENTS OF THE INVENTION

Practically and presently preferred embodiments of the present invention will be illustrated by following Examples.

Preparation of Solid Bases

Solid Base A-1

An activated alumina of 42-200 mesh (NKHD-24, a trade name of Sumitomo Chemical Co., Ltd.) (26.5 g) was added to a suspension of magnesium hydroxide (2.5 g) in water (50 g), and the aqueous mixture was evaporated at about 70° C. with a rotary evaporator.

The residue was stirred at 500° C. for 2 hours in a nitrogen atmosphere and cooled to 290° C. Then, metal potassium (2.0 g) was added, and the mixture was stirred at the same temperature for 0.2 hour followed by cooling to room temperature to obtain Solid Base A-1 (26.2 g).

Solid Base A-2

In the same manner as in the preparation of Solid Base A-1, but using calcium hydroxide (2.5 g) in place of magnesium hydroxide, Solid Base A-2 (27.5 g) was prepared.

Solid Base A-3

In the same manner as in the preparation of Solid Base A-1, but using barium hydroxide (2.5 g) in place of magnesium hydroxide, Solid Base A-3 (27 g) was prepared.

Solid Base A-4

In the same manner as in the preparation of Solid Base A-1, but using magnesium oxide (2.5 g) in place of magnesium hydroxide, Solid Base A-4 (26.8 g) was prepared.

EXAMPLE 1

In a 600 ml autoclave equipped with a magnetic stirrer, Solid Base A-1 (0.43 g) and cumene (240 g) were charged under nitrogen, heated to 160° C. while stirring at 1000 rpm and then reacted at the same temperature for 3 hours while supplying ethylene gas under pressure of 10 kg/cm$^2$G. to produce tert.-amylbenzene (hereinafter referred to as "TAB").

After the reaction, the autoclave was cooled, and the catalyst was filtered off. The product was analyzed with gas chromatography. The results are shown in Table 1.

The selectivity of TAB is calculated according to the following equation:

$$\text{Selectivity (\%)} = \frac{\text{Amount of produced } TAB \text{ (mole)} \times 100}{\text{Total amount of all produced alkyl-substituted compounds (mole)}}$$

EXAMPLE 2

In the same manner as in Example 1, except that the reaction temperature was 100° C. and 0.48 g of Solid Base A-1 was used, the alkylation was carried out. The results are shown in Table 1.

EXAMPLES 3-5

In the same manner as in Example 1, but using one of Solid Bases A-2, A-3 and A-4, the alkylation was carried out. The results are shown in Table 1.

In Examples 1-5, the catalysts were still active at the end of the reaction and the alkylation could be further carried out by using the same catalysts.

Comparative Examples 1

To a 200 ml autoclave equipped with a magnetic stirrer, anhydrous potassium carbonate which had been calcined at 400° C. for 2 hours in a nitrogen atmosphere (8.19 g), metal sodium (0.30 g) and cumene (26.7 g) were charged under nitrogen, heated to 190° C. while stirring at 1000 rpm then stirred at the same temperature for 2 hours.

After cooling the autoclave, additional cumene (53.3 g) was added and the mixture was heated to 160° C. while stirring at 1000 rpm and the reacted at the same temperature for 3 hours while supplying ethylene gas under pressure of 10 kg/cm²G.

After the reaction, the product was analyzed in the same manner as in Example 1. The conversion of cumene was 19.4% and the selectivity of TAB was 73.9%.

TABLE 1

| Example No. | Solid Base (g) | Reaction time (hrs) | Conversion of cumene (%) | Selectivity of TAB (%) |
| --- | --- | --- | --- | --- |
| 1 | A-1 (0.43) | 3 | 99.9 | 98.18 |
| 2 | A-1 (0.48) | 3 | 99.8 | 97.90 |
| 3 | A-2 (0.46) | 3 | 99.0 | 97.51 |
| 4 | A-3 (0.46) | 3 | 97.7 | 97.93 |
| 5 | A-4 (0.42) | 3 | 99.9 | 98.45 |
| Comp. 1 | Mixture (8.49) | 3 | 19.4 | 73.9 |

EXAMPLE 6

In a 300 ml autoclave equipped with a magnetic stirrer, Solid Base A-1 (2.86 g) and toluene (80 g) were charged under nitrogen and then liquid propylene (70 ml) was injected under pressure. The mixture was stirred at 164° C. for 6 hours to obtain isobutylbenzene (hereinafter referred to as "IBB").

After the reaction, the product was analyzed in the same manner as in Example 1. The results are shown in Table 2. The selectivity of IBB is calculated according to the following equation:

$$\text{Selectivity (\%)} = \frac{\text{Amount of produced } IBB \text{ (mole)} \times 100}{\text{Total amount of all produced alkyl-substituted compounds (mole)}}$$

EXAMPLES 7-9

In the same manner as in Example 6, but using one of Solid Bases A-2, A-3 and A-4 in place of Solid Base A-1, the reaction was carried out. The results are shown in Table 2.

In Examples 6-9, the catalysts were still active at the end of the reaction and the alkylation could be further carried out by using the same catalysts.

Comparative Example 2

In a 200 ml autoclave equipped with a magnetic stirrer, anhydrous potassium carbonate which had been calcined at 400° C. for 2 hours in a nitrogen atmosphere (8.45 g), metal sodium (0.3 g) and toluene (26.6 g) were charged under nitrogen, heated to 190° C. while stirring at 1000 rpm and then stirred at the same temperature for 2 hours.

After cooling the autoclave, additional toluene (53.2 g) was added and liquid propylene (70 ml) was injected under pressure. Then, the mixture was stirred at 160° C. for 6 hours.

After the reaction, the product was analyzed in the same manner as in Example 1. The results are shown in Table 2.

TABLE 2

| Example No. | Solid Base (g) | Conversion of toluene (%) | Selectivity of IBB (%) |
| --- | --- | --- | --- |
| 6 | A-1 (2.86) | 22.5 | 90.3 |
| 7 | A-2 (3.25) | 24.0 | 90.9 |
| 8 | A-3 (3.06) | 23.1 | 89.5 |
| 9 | A-4 (3.21) | 19.5 | 90.7 |
| Comp. 2 | Mixture (8.75) | 3.5 | 89.2 |

Preparation of Solid Bases

Solid Base B-1

An activated alumina of 42-200 mesh (NKHD-24, a trade name of Sumitomo Chemical Co., Ltd.) (26.5 g) was added to a suspension of magnesium oxide (2.5 g) in water (50 g), and the aqueous mixture was evaporated at about 70° C. with a rotary evaporator.

The residue was stirred at 500° C. for 1.5 hours in a nitrogen atmosphere and cooled to 360° C. Then, potassium hydride (2.71 g) was added, and the mixture was stirred at the same temperature for 0.4 hour followed by cooling to room temperature to obtain Solid Base B-1 (25.0 g).

Solid Base B-2

In the same manner as in the preparation of Solid Base B-1 but using 17.25 g of the same activated alumina, and magnesium hydroxide (1.73 g) in place of magnesium oxide and potassium hydride (1.71 g), Solid Base B-2 (1.71 g) was prepared.

Solid Base B-3

The same activated alumina as used in the preparation of Solid Base B-1 (26.5 g) and magnesium acetate [Mg(OAc)$_2$.4H$_2$O] (14.0 g) were stirred at 470° C. for 5 hours in the air. Then, in a nitrogen atmosphere, potassium hydride (2.40 g) was added at 360° C., and the mixture was stirred at the same temperature for 0.4 hour followed by cooling to room temperature to obtain Solid Base B-3.

Solid Base B-4

In the same manner as in the preparation of Solid Base B-1, but stirring the residue (before the addition of potassium hydride) at 360° C. and using 2.74 g of potassium hydride, Solid Base B-4 was prepared.

Solid Base B-5

In the same manner as in the preparation of Solid Base B-1, but stirring the residue (before the addition of potassium hydride) at 700° C. and using 3.12 g of potassium hydride, Solid Base B-5 was prepared.

Solid Base B-6

In the same manner as in the preparation of Solid Base B-1, but using magnesium hydroxide (2.5 g) in place of magnesium oxide and using 2.45 g of potassium hydride, Solid Base B-6 was prepared.

Solid Base B-7

In the same manner as in the preparation of Solid Base B-1, but using barium hydroxide [$Ba(OH)_2.8H_2O$] (4.60 g) in place of magnesium oxide and 2.57 g of potassium hydride, Solid Base B-7 was prepared.

Solid Base B-8

In the same manner as in the preparation of Solid Base B-1, the suspension of alumina (26.5 g) and magnesium oxide (2.5 g) was evaporated.

The residue was heated in a quartz tube at 1000° C. for 1.5 hours in a nitrogen atmosphere. Then, potassium hydride (3.09 g) was added at 360° C., and the mixture was stirred at the same temperature for 0.4 hour followed by cooling to room temperature to obtain Solid Base B-8.

Solid Base B-9

In the same manner as in the preparation of Solid Base B-1, but using 2.46 g of potassium hydride, Solid Base B-9 was prepared.

EXAMPLES 10–16 AND COMPARATIVE EXAMPLE 3

In the same manner as in Example 1, but using one of Solid Bases B-1 to B-8 in place of Solid Base A-1 and carrying out the reaction at 100° C. under the conditions shown in Table 3, the alkylation was carried out. The results are shown in Table 3.

In Examples 10–16, the catalysts were still active at the end of the reaction and the alkylation could be further carried out by using the same catalysts.

TABLE 3

| Example No. | Solid Base (g) | Reaction time (hrs) | Conversion of cumene (%) | Selectivity of TAB (%) |
|---|---|---|---|---|
| 10 | B-1 (0.38) | 1.0 | 91.2 | 99.4 |
| 11 | B-2 (0.50) | 1.0 | 95.2 | 99.5 |
| 12 | B-3 (0.41) | 1.0 | 89.8 | 99.8 |
| 13 | B-4 (0.46) | 1.0 | 90.8 | 99.8 |
| 14 | B-5 (0.42) | 1.0 | 8.1 | 88.4 |
| 15 | B-6 (0.44) | 1.5 | 92.0 | 99.5 |
| 16 | B-7 (0.42) | 1.5 | 95.9 | 99.0 |
| Comp. 3 | B-8 (1.47) | 1.0 | 5.2 | 78.0 |
| Comp. 1 | Mixture (8.49) | 3.0 | 19.4 | 73.9 |

EXAMPLES 17 AND 18

In the same manner as in Example 6, but using Solid Base B-6 or B-9 in place of Solid Base A-1, the alkylation was carried out.

After the reaction, the product was analyzed in the same manner as in Example 1. The results are shown in Table 4.

In Example 17 and 18, the catalysts were still active at the end of the reaction and the alkylation could be further carrier out by using the same catalysts.

TABLE 4

| Example No. | Solid Base (g) | Conversion of toluene (%) | Selectivity of IBB (%) |
|---|---|---|---|
| 17 | B-9 (3.18) | 35.6 | 89.7 |
| 18 | B-6 (2.84) | 35.0 | 90.1 |
| Comp. 2 | Mixture (8.75) | 3.5 | 89.2 |

What is claimed is:

1. A process for preparing an alkyl-substituted hydrocarbon comprising alkylating an alkylaromatic hydrocarbon having at least one hydrogen atom on an alpha-carbon in a side chain with an olefin in the presence of a solid base which is obtainable by treating an alumina with at least one compound of an alkaline earth metal at a temperature of from 200° to 800° C. and then with at least one compound selected from the group consisting of an alkali metal and an alkali metal hydride in an inert gas at a temperature of from 200° to 800° C.

2. The process according to claim 1, wherein the solid base is one which is obtainable by treating the alumina with said at least one compound of an alkaline earth metal and then with an alkali metal.

3. The process according to claim 1, wherein the solid base is one which is obtainable by treating the alumina with said at least one compound of an alkaline earth metal and then with an alkali metal hydride.

4. The process according to claim 1, wherein the solid base is one obtainable by treating the alumina with said at least one compound of an alkaline earth metal and then successively with at least one compound selected from the group consisting of an alkali metal and an alkali metal hydride at a temperature of from 200° to 450° C.

5. The process according to claim 1, wherein said at least one compound of an alkaline earth metal is selected from the group consisting of an oxide, a hydroxide, an alkoxide and an acetate of the alkaline earth metal.

6. The process according to claim 1, wherein said at least one compound of an alkaline earth metal is selected from the group consisting of an oxide and a hydroxide of the alkaline earth metal.

7. The process according to claim 1, wherein the solid base is one obtainable by treating the alumina with said at least one compound of an alkaline earth metal at a temperature of from 250° to 600° C.

8. The process according to claim 1, wherein the amount of said at least one compound of an alkaline earth metal used is from 5 to 40% by weight based on the weight of the alumina.

9. The process according to claim 1, wherein the amount of said at least one compound is selected from the group consisting of an alkali metal and an alkali metal hydride used is from 2 to 15% by weight based on the weight of the alumina.

10. The process according to claim 1, wherein said at least one compound of an alkaline earth metal is selected from the group consisting of magnesium oxide, magnesium hydroxide, calcium hydroxide, barium hydroxide and magnesium acetate.

11. The process according to claim 1, wherein the alkali metal is at least one selected from the group consisting of sodium and potassium 12. The process according to claim 11, wherein the alkali metal is potassium.

13. The process according to claim 1, wherein the alkali metal hydride is at least one member selected from the group consisting of sodium hydride and potassium hydride.

14. The process according to claim 13, wherein the alkali metal hydride is potassium hydride.

15. The process according to claim 1, wherein said alkylaromatic hydrocarbon is selected from the group consisting of toluene, ethylbenzene, isopropylbenzene, n-propylbenzene, n-butylbenzene, sec.-butylbenzene, isobutylbenzene, xylene, cymene, diisopropylbenzene, methylnaphthalene, tetrahydronaphthalene, and indan.

16. The process according to claim 15, wherein the alkylaromatic hydrocarbon is at least one member selected from the group consisting of toluene and isopropylbenzene.

17. The process according to claim 1, wherein the olefin has 2 to 20 carbon atoms.

18. The process according to claim 17, wherein the olefin is selected from the group consisting of ethylene and propylene.

19. The process according to claim 1, wherein an alkylation temperature is from 20° to 200° C.

* * * * *